(12) United States Patent
Levine et al.

(10) Patent No.: US 6,171,826 B1
(45) Date of Patent: Jan. 9, 2001

(54) METHODS OF CONTROLLING BETA DIMER FORMATION IN HEMOGLOBIN

(75) Inventors: Joseph D. Levine, Louisville; Izydor A. Apostol, Boulder, both of CO (US)

(73) Assignee: Baxter Biotech Technology Sarl, Neuchatel (CH)

( * ) Notice: Under 35 U.S.C. 154(b), the term of this patent shall be extended for 0 days.

(21) Appl. No.: 09/230,603

(22) PCT Filed: Aug. 1, 1997

(86) PCT No.: PCT/US97/13564

§ 371 Date: May 14, 1999

§ 102(e) Date: May 14, 1999

(87) PCT Pub. No.: WO98/05773

PCT Pub. Date: Feb. 12, 1998

Related U.S. Application Data

(60) Provisional application No. 60/023,211, filed on Aug. 2, 1996.

(51) Int. Cl.$^7$ ............................ C12P 21/06; C07K 14/805
(52) U.S. Cl. ................................. 435/69.6; 530/385
(58) Field of Search ............................ 435/69.6; 530/385

(56) References Cited

U.S. PATENT DOCUMENTS

| | | | |
|---|---|---|---|
| 5,545,727 | 8/1996 | Hoffman et al. | 536/234 |
| 5,563,254 | 10/1996 | Hoffman et al. | 536/23.5 |
| 5,578,564 | 11/1996 | Chiver et al. | 514/6 |
| 5,840,851 | 11/1998 | Plomer et al. | 530/385 |

FOREIGN PATENT DOCUMENTS

| | | | |
|---|---|---|---|
| 93/09143 | 5/1993 | (WO) . | |
| 95/14038 | 5/1995 | (WO) | 14/805 |
| 95/24213 | 9/1995 | (WO) | 38/42 |
| 97/04110 | 2/1997 | (WO) | 15/63 |
| 98/05773 | 2/1998 | (WO) | 14/805 |

OTHER PUBLICATIONS

Russu, et al., A Proton Nuclear Magnetic Resonance Investigation of Histidyl Residues in Human Normal Adult Hemoglobin, Biochemistry, 1982, vol. 21, pp. 5031–5043.

Hirel, et al., Extent of N–terminal Methionine Excision From *Escherichia coli* Proteins is Governed by the Side–chain Length of the Penultimate Amino Acid, Proc. Natl, Acad. Sci., vol. 86, pp. 8247–8251, Nov. 1989.

Climent, et al., Derivatization of γ–Glutamyl Semialdehyde Residues in Oxidized Proteins by Fluoresceinamine, Analytical Biochemistry, vol. 182, pp. 226–232, 1989.

Stadtman, et al., Metal–Catalyzed Oxidation of Proteins, The Journal of Biological Chemistry, vol. 266, No. 4, pp. 2005–2008, 1991.

Schöneich, et al., Iron–thiolate Induced Oxidation of Methionine to Methionine Sulfoxide in Small Model Peptides. Intramolecular Catalysis By Histidine, Biochimica et Biophysica Acta, vol. 1158, ppg. 307, 1993.

Shibayama, et al., Oxygen Equilibrium Properties of Nickel (II)—Iron (II Hybrid Hemoglobins Cross–Linked between 82β1 and 82β2 Lysyl Residues by Bis (3,5–dibromosalicyl) fumarate: Determination of the First Two–Step Microscopic Adair Constants for Human Hemoglobin, Biochemistry, vol. 34, pp. 4773–4780, 1995.

Brown, et al., Highly Specific Oxidative Cross–Linking of Proteins Mediated by a Nickel–Peptide Complex, Biochemistry, vol. 34, pp. 4733–4739, 1995.

Dumoulin, et al., Loss of Allosteric Behaviour in Recombinant Hemoglobin $\alpha_2\beta_2$92 (F8) His→Ala: Restoration Upon Addition of Strong Effectors, FEBS Letters, vol. 374, pp. 39–42, 1995.

Levin, et al., Methionine Residues as Endogenous Antioxidants in Proteins, Proc. Natl. Acad. Sci., vol. 93, pp. 15036–15040, Dec. 1996.

Bravo, et al., Identification of a Novel Bond Between a Histidine and the Essential Tyrosine in Catalas HPII of *Escherichia Coli*, Protein Science, vol. 6, pp. 1016–1923, 1997.

Levine, et al., Identification of a Nickel (II) Binding Site on hemoglobin Which Confers Susceptibility to Oxidative Deamination and Intramolecular Cross–Linking, the Journal of Biological Chemistry, vol. 273, No. 21, pp. 13037–13046, 1998.

*Primary Examiner*—Karen Cochrane Carlson
(74) *Attorney, Agent, or Firm*—Senniger, Powers, Leavitt & Roedel

(57) ABSTRACT

The present invention relates to methods of controlling beta dimer formation in hemoglobin solutions by altering the metal binding site adjacent to the N-terminus of beta globins. The invention further relates to methods of producing stable, intramolecularly crosslinked beta globins by exposure to Ni(II) and oxone.

13 Claims, 3 Drawing Sheets

METHODS OF CONTROLLING BETA DIMER FORMATION IN HEMOGLOBIN

This appln is a 371 of PCT/US97/13564 filed Aug. 1, 1997 and also claims the benefit of U.S. Provisional No. 60/023,211 filed Aug. 2, 1996.

FIELD OF THE INVENTION

The present invention generally relates to expression of recombinant hemoglobin, and more particularly to methods of controlling beta dimer formation during the recombinant expression of the beta subunit.

BACKGROUND OF THE INVENTION

It is not always practical or safe to transfuse a patient with donated blood. In these situations, use of a red blood cell substitute is desirable. When human blood is not available or the risk of transfusion is too great, plasma expanders can be administered. However, plasma expanders, such as colloid and crystalloid solutions, replace only blood volume, and not oxygen carrying capacity. In situations where blood is not available for transfusion, a red blood cell substitute that can transport oxygen in addition to providing replacement is desirable.

Hemogloblin has been identified as a desirable red blood cell substitute. Hemoglobin (also referred to herein as "Hb") is the oxygen-carrying component of blood. Hemoglobin circulates through the bloodstream inside small enucleate cells called erythrocytes (red blood cells). Hemoglobin is a protein constructed from four associated polypeptide chains, and bearing prosthetic groups known as hemes. The erythrocyte helps maintain hemoglobin in its reduced, functional form. The heme iron atom is susceptible to oxidation, but may be reduced again by one of two enzyme systems within the erythrocyte, the cytochrome $b_5$ and glutathione reduction systems.

Hemoglobin binds oxygen at a respiratory surface (skin, gills, trachea, lung, etc.) and transports the oxygen to inner tissues, where it is released and used for metabolism. In nature, low molecular weight hemoglobins (16–120 kilodaltons) tend to be enclosed in circulating red blood cells, while the larger polymeric hemoglobins circulate freely in the blood or hemolymph.

The structure of hemoglobin is well known as described in Bunn & Forget, eds., *Hemoglobin: Molecular, Genetic and Clinical Aspects* (W.B. Saunders Co., Philadelphia, Pa.: 1986) and Fermi & Perutz "Hemoglobin and Myoglobin," in Phillips and Richards, *Atlas of Molecular Structures in Biology* (Clarendon Press: 1981).

About 92% of normal adult human hemolysate is Hb $A_o$ (designated alpha$_2$ beta$_2$ because it comprises two alpha and two beta chains). In a hemoglobin tetramer, each alpha subunit is associated with a beta subunit to form a stable alpha/beta dimer, two of which in turn associate to form the tetramer. The subunits are noncovalently associated through Van der Waals forces, hydrogen bonds and salt bridges. The amino acid sequences of the alpha and beta globin polypeptide chains of Hb $A_o$ are given in Table 1 of PCT Publication No. WO 93/09143. The wild-type alpha chain consists of 141 amino acids. The iron atom of the heme (ferroprotoporphyrin IX) group is bound covalently to the imidazole of His 87 (the "proximal histidine"). The wild-type beta chain is 146 residues long and heme is bound to it at His 92.

The human alpha and beta globin genes reside on chromosomes 16 and 11, respectively. Bunn and Forget, infra at 172. Both genes have been cloned and sequenced, Liebhaber, et al., *PNAS* 77: 7054–58 (1980) (alpha-globin genomic DNA); Marotta, et al., *J. Biol. Chem.*, 252: 5040–53 (1977) (beta globin cDNA); Lawn, et al., *Cell*, 21:647 (1980) (beta globin genomic DNA).

Hemoglobin exhibits cooperative binding of oxygen by the four subunits of the hemoglobin molecule (the two alpha globins and two beta globins in the case of Hb $A_o$), and this cooperativity greatly facilitates efficient oxygen transport. Cooperativity, achieved by the so-called heme-heme interaction, allows hemoglobin to vary its affinity for oxygen. Cooperativity can also be determined using the oxygen dissociation curve (described below) and is generally reported as the Hill coefficient, "n" or "$n_{max}$." Hemoglobin reversibly binds up to four moles of oxygen per mole of hemoglobin.

Oxygen-carrying compounds are frequently compared by means of a device known as an oxygen dissociation curve. This curve is obtained when, for a given oxygen carrier, oxygen saturation or content is graphed against the partial pressure of oxygen. For Hb, the percentage of saturation increases with partial pressure according to a sigmoidal relationship. The $P_{50}$ is the partial pressure at which the oxygen-carrying species is half saturated with oxygen. It is thus a measure of oxygen-binding affinity; the higher the $P_{50}$, the more readily oxygen is released.

The production of recombinant hemoglobin particularly in *E.coli* can lead to multiple species of recombinant hemoglobin. For example, in producing recombinant beta globins in bacterial systems, particularly *E.coli*, the beta globin can be expressed as a mixture of monomeric and dimeric beta globins. Thus, a need exists to control the formation of dimeric beta globins. The present invention satisfies this need and provides related advantages as well.

SUMMARY OF THE INVENTION

The present invention relates to methods of controlling beta dimer formation in a hemoglobin solution. The methods are accomplished by altering a metal binding site, particularly a nickel binding site, on a beta globin or globin-like polypeptide to prevent or reduce said beta dimer formation. The methods are particularly suitable in the recombinant production of hemoglobin. Preferably, the metal binding site is the histidine adjacent to the N-terminal amino acid of the beta globin or globin-like polypeptide. For example, the histidine can be substituted with leucine or alanine in order to control the formation of beta dimers.

The present invention is further directed to methods of producing stable, intramolecularly crosslinked beta dimers by adding Ni(II) and oxone to a hemoglobin solution. Such methods will produce stable dimers within the hemoglobin contained in the solution between globins containing histidine adjacent to the N-terminal residue (hereinafter also referred to as "His2"). The hemoglobin can be derived from any source, for example, those sources described in WO 95/24213, published on Sep. 14, 1995, and incorporated herein by reference.

DETAILED DESCRIPTION OF THE INVENTION

Figure 1:
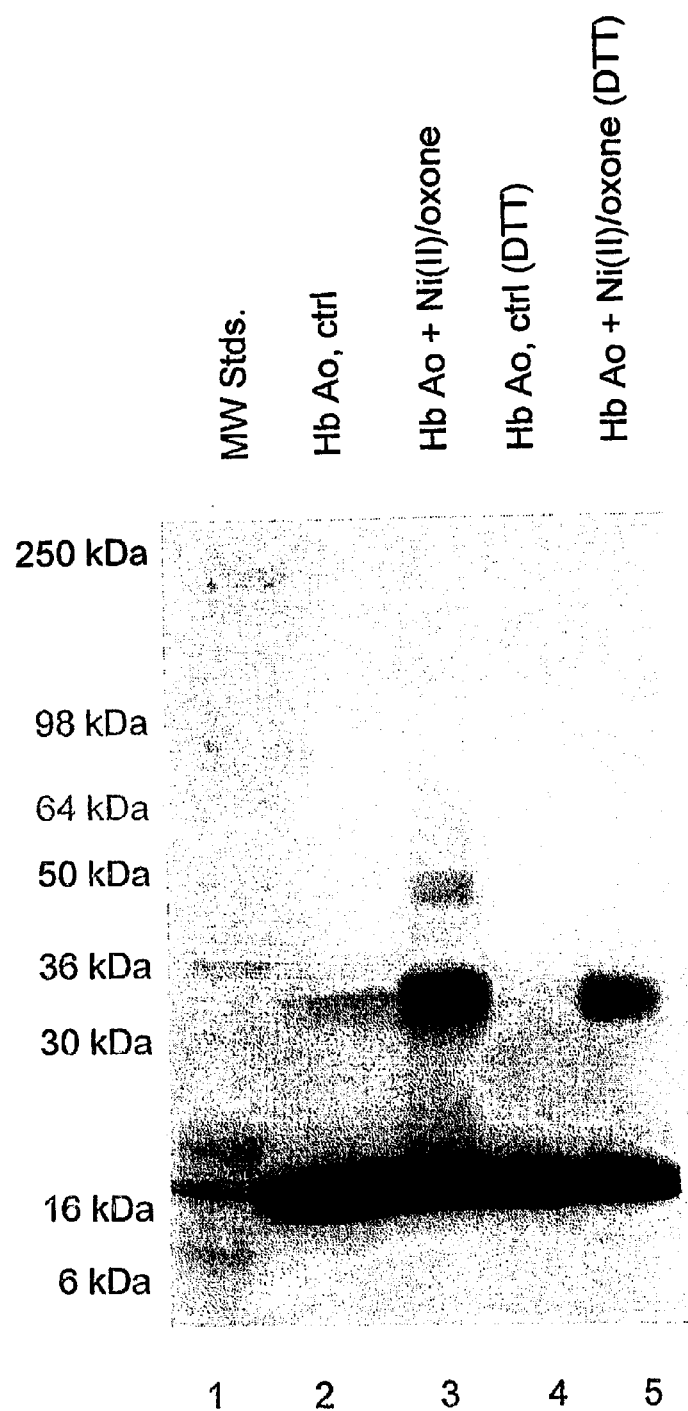
FIG. 1 shows the SDS-PAGE of human hemoglobin $A_o$ before and after reaction with Ni(II)/oxone. Gel contents: protein size markers (lane 1), Hb $A_o$ before reaction under reducing conditions with DTT (lane 4), Hb $A_o$ after reaction under reducing conditions with DTT (lane 5).
Figure 2:
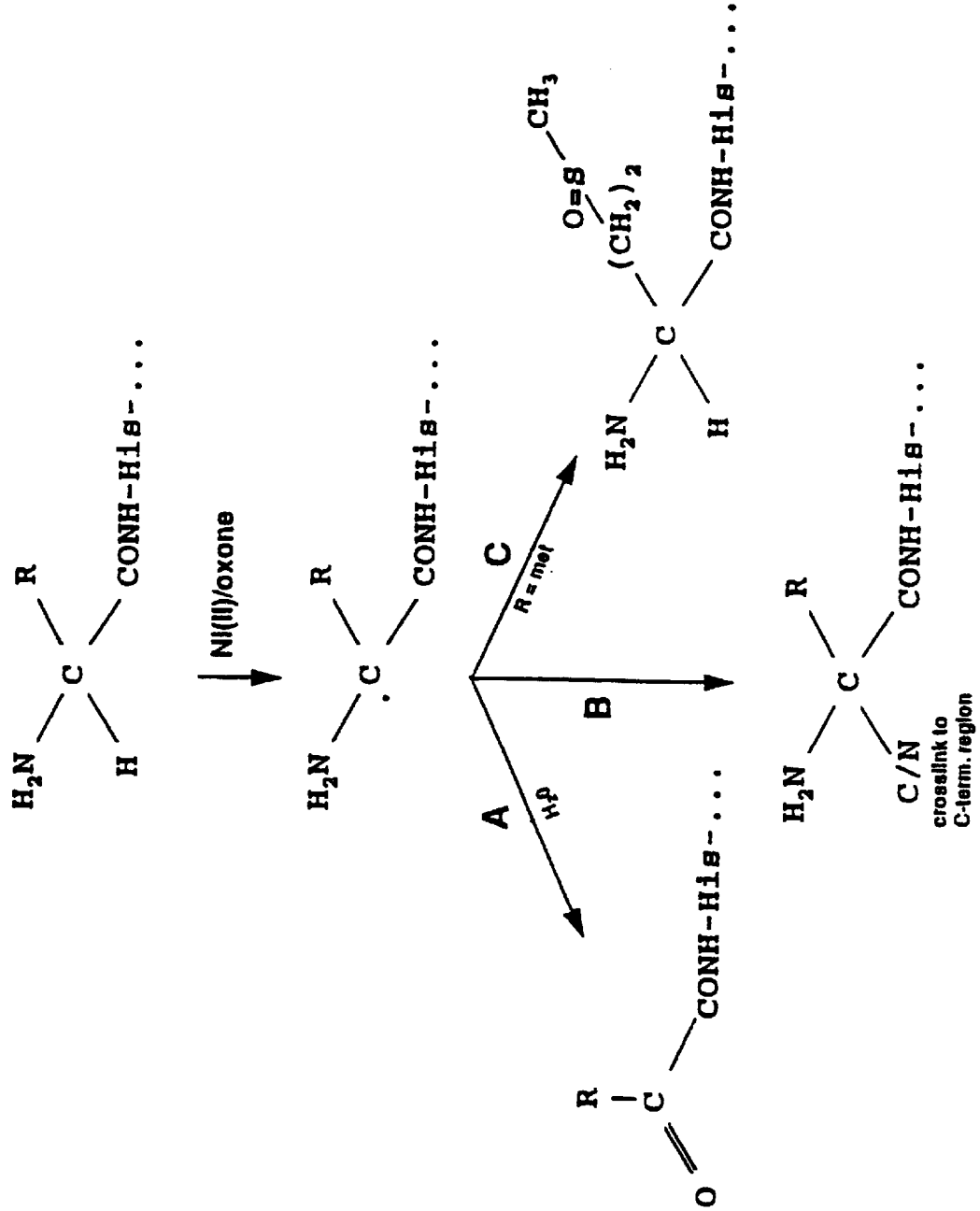
FIG. 2 shows the proposed scheme of oxidative damage occurring at the N-terminus of the beta chain in hemoglobins containing His residue in position 2 (His2).

The present invention generally relates to methods of controlling beta dimer formation during the production of recombinant hemoglobin. The invention is based on the discovery that the beta chain of human hemoglobin contains a histidine adjacent to the N-terminal amino acid that confers susceptibility to metal catalyzed oxidation leading to the formation of stable beta globin dimers.

Transition metal catalyzed oxidative damage to proteins has been implicated in a variety of adverse physiological processes including aging, arteriosclerosis and ischemic reperfusion. The metal binding site-specific nature of metal catalyzed oxidation of proteins has been well established (Amici et al., *J. Biol. Chem.* 264:3341 (1989); Stadtman, *Ann. Rev. Biochem.* 62:797–821 (1993)). Oxidative modification of proteins in vivo have been postulated to produce carbonyl groups on amino acid side chains, including the formation of gamma-glutamyl semialdehyde from arginine (Climent et al., *Anal. Biochem.* 182:226 (1989) and 2-amino adipic semialdehyde from lysine (Stadtman & Oliver, *J. Biol. Chem.* 266:2005 (1991)). Investigators have used model systems employing Fe(II), and $H_2O_2$ to study oxidative modification of proteins and peptides in vitro, and the physiological relevance of such Fenton chemistry models in elucidating mechanisms of in vivo oxidation of proteins is widely accepted (Stadtman & Oliver, supra; Schoneich et al., *Biochim. Biophys. Acta* 1158:307 (1993)).

Oxidative intermolecular crosslinking of other proteins associatively complexed in solution has been recently reported (Brown et al., *Biochemistry* 34:4733–4739 (1995) in which an exogenous tripeptide ($NH_2$-Gly-Gly-His-COOH) was added to the proteins to serve as a nickel binding site for the peracid mediated formation of a high valent nickel complex. This complex propagated covalent bond formation between the associated proteins, presumably by attack of aromatic amino acids. Intramolecular oxidations promoted by high valent nickel and iron complexes directed to the amino and/or carboxyl termini of peptides with vicinal histidine residues has also been reported in Schoenich et al., *Biochimica et Biophysica Acta*. 1158:307–322 (1993).

Hemoglobin in contrast contains metal binding sites without the need to insert such sites. However, previously, the investigation of metal catalyzed protein oxidation of hemoglobin and other heme proteins, has been complicated by the catalytic interaction of the heme iron with peroxides. This reaction can produce significant heme oxidation and protein degradation through the formation of the highly unstable ferryl-heme species. The present invention, however, relates to a reaction of hemoglobin and oxidants under conditions in which oxidative crosslinks between protein subunits can be generated without causing appreciable heme iron oxidation, protein denaturation, or aggregation.

These metal binding sites appear to promote covalent bond formation between the beta globin subunits in the presence of nickel ions and an oxidant. Covalent bond formation can, in fact, be driven in vitro by potassium peroxymonosulate known as "oxone." The beta globin dimerization results in relatively little formation (<5%) of multi-tetrameric (i.e., intermolecular crosslinked) hemoglobin species. The dimers are therefore predominantly intramolecularly crosslinked with no disulfide bond involvement.

As noted above, a metal binding site on hemoglobin appears to promote covalent bond formation between the beta globin subunits upon addition of oxone in the presence of nickel. This reaction also results in a substanial yield of a modification which has been identified as oxidative deamination of the beta globin amino terminus, generating in its place a beta-ketoamide. Results from the present studies indicate the beta globin His2 is required for active nickel complexation, oxidative deamination, and intramolecular crosslinking.

It has now been discovered that a reaction of human hemoglobin $A_o$ with oxone in the presence of nickel (II) ions produces predominantly intramolecular crosslinking of the beta globins of the protein and significant oxidative deamination of the beta globin amino termini. The oxidative conditions used were not sufficiently harsh to oxidize the ferrous hemes of the carbon monoxide liganded hemoglobin, and no catlytic activity of the heme centers appears to be involved. No evidence was found that the alpha globins are similarly susceptible to N-terminal oxidative deamination under the conditions used. One primary sequence difference between the beta and alpha chains of human hemoglobin is that the beta chain contains a histidine adjacent to the N-terminal amino acid.

alpha globin V-LSPADK . . . (SEQ ID No:1)
beta globin VHLTPEEK . . . (SEQ ID No:2)

It is believed that histidine at this position may confer susceptibility to metal catalyzed oxidation. Results with different recombinant hemoglobin variants confirm that the histidine at position 2 is required for both Ni(II) catalyzed oxidative deamination of the beta globin amino terminus, and intramolecular crosslinking of the beta globins. It was found that a spectrophotometrically observable absorbance change induced in hemoglobin by complexation with Ni(II) is absent in hemoglobins lacking a histidine at position 2 of the beta globins provides further evidence that the beta globin His2 is an essential part of a unique, redox active Ni(II) complexation site on hemoglobin.

Experimental results suggest that Ni(II) catalyzed oxidative intramolecular crosslinking of the beta globins occurs between the N-terminus of one and the C-terminal region of the other globin. Peptide mapping did not, however, provide identification of a primary crosslink, but rather indicated the heterogeneous character of crosslinks produced by the reaction. Characterization of an amine doublet of crosslinked peptides found following sodium cyanoborohydride treatment of the still-native state hemoglobin reaction appears consistent with a Schiff's base reduction, resulting in a secondary amine bond between the oxidatively deaminated beta globin terminus and the epsilon-amino group of Lys144 at an opposing beta globin from within the same protein molecule. However, recombinant hemoglobin variants lacking lysine at position 144 remain susceptible to beta globin dimerization. The reported structure of R-state hemoglobin indicates close spatial contact between the amino terminus and the carboxyl terminus of opposing beta globins in the hemoglobin tetramer (Baldwin, *J. Mol. Biol.* 136:103 (1980)).

Hemoglobin variants containing substitutions: His143 Ala, Tyr145His, or deletion of His146 all exhibited comparable susceptibility to crosslinking, suggesting no specific side chain of C-terminal residue is strictly required. Two recombinant hemoglobin variants containing 3, or 4 amino acid deletions at the C-terminus, respectively, did show significantly decreased susceptibility for dimerization. This may be due to steric considerations, in that the new C-terminal region of these variants is likely no longer in close enough proximity contact with the beta globin N-terminus for crosslink formation.

From these findings, it is believed that histidine at beta globin position 2 confers susceptibility, under oxidizing conditions, to the nickel catalyzed formation of a carbon-centered radical at the alpha-carbon of the beta globin amino terminal residue, analogous to that proposed by Stadtman on the epsilon carbon in the iron catalyzed deamination of lysine . The "activated" alpha carbon can react in one of three ways. First, the radical can react immediately with water resulting in oxidative deamination, analogous to that proposed by Stadtman. Second, the radical can attack a variety of sites on a spatially adjacent beta C-terminal region, leading to a heterogeneous set of carbon-carbon and/or carbon-nitrogen bonds. The numerous combinations of potential products resulting from this pathway may, in part, explain the difficulty in identifying specific N-terminal to C-terminal region crosslinked peptides. A similar type of labile bond has recently been proposed to form between the beta carbon of the essential tyrosine and nitrogen of histidine in catalase HPII of *E. coli* (Bravo et al., *Protein Sci*. 6:1016 (1997)). Finally, in the case when the N-terminal residue is methionine, the radical can transfer to the side chain sulfur atom leading to the formation of methionine sulfoxide, effectively "quenching" oxidative deamination. This finding provides a unique example of methionine serving as an intrinsic antioxidant in a protein, a role recently postulated by Levine et al., *Proc. Nat'l Acad. Sci. U.S.A.*, 93:15036 (1996).

Although beta dimerization can be useful for certain hemoglobin applications, it is not always desirable. Therefore, in one aspect, the present invention relates to methods of preventing the formation of such beta dimers. Such methods are accomplished by mutations in the beta globin. For example, in one embodiment, the histidine adjacent to the N-terminal amino acid in the beta globin can be substituted with one or more amino acids so that the expressed protein does not have a histidine in the second position from the N-terminus. Similarly, one or more amino acids can be inserted between the N-terminal amino acid and histidine as long as the inserted amino acid is not an amino acid directing N-terminal Met removal, for example, alanine, glycine, proline, serine, threonine, valine and cysteine if the beta globin in expressed by an *E.coli* host cell (Hirel et al., *Proc. Nat'l Acad. Sci. U.S.A.*, 86:8247–51 (1989)). For example, in the *E.coli* system, the initating methionine (Met) residue is quantitatively removed by endogenous *E.coli* methionylaminopeptidase when the second amino acid expressed is alanine. Therefore, if alanine is inserted in front of the histidine, the resulting expressed protein would contain a histidine at the second position due to the cleavage of Met. Methods for the addition or substitution of amino acids can be accomplished by means known in the art or as described in the Examples below.

The present invention further relates to the mutated beta globins and to the nucleic acids useful for the expression of such mutations. Such nucleic acids can be used to construct plasmids to be inserted into appropriate recombinant host cells according to conventional methods or as described in the Examples below.

Briefly, plasmids were constructed with various mutations in beta and used to transform *E.coli* host cells. Crosslinking reactions were carried out using $NiCl_2$, followed by the addition of oxone. The reaction of the native hemoglobin (i.e., with histidine at position 2—His2) in solution with Ni(II) and oxone resulted in the formation of intramolecular, dimeric beta globin. This reaction is blocked by inclusion of EDTA in the reaction mixture, as well as by substitution of the His2 in the beta globin with Leu or Ala. These results indicate that the beta globin His2 can serve as a binding site for a high valent nickel complex. This complex promotes predominantly intramolecular crosslinking to form stable beta dimers.

The present invention is also directed to any suitable host cell containing a desired beta globin mutation. Suitable host cells include, for example, bacterial, yeast, mammalian, reptilian and insect cells. *E. coli* cells are particularly useful for expressing the novel polypeptides. Preferably, when multiple subunits are expressed in bacteria, it is desirable, but not required, that the subunits be co-expressed in the same cell polycistronically as described in WO 93/09143. The use of a single promoter is preferable in *E. coli* to drive the expression of the genes encoding the desired proteins.

The recombinant hemoglobin containing the beta mutations of the present invention can be used for a number of in vitro or in vivo applications. Such in vitro applications include, for example, the delivery of oxygen by compositions of the instant invention for the enhancement of cell growth in cell culture by maintaining oxygen levels in vitro (DiSorbo and Reeves, PCT publication WO 94/22482, herein incorporated by reference). Moreover, the hemoglobins of the instant invention can be used to remove oxygen from solutions requiring the removal of oxygen (Bonaventura and Bonaventura, U.S. Pat. No. 4,343,715, incorporated herein by reference) and as reference standards for analytical assays and instrumentation (Chiang, U.S. Pat. No. 5,320,965, incorporated herein by reference) and other such in vitro applications known to those of skill in the art.

In a further embodiment, the hemoglobins of the present invention can be formulated for use in therapeutic applications. Example formulations suitable for the hemoglobin of the instant invention are described in Milne, et al., WO 95/14038 and Gerber et al., PCT/US95/10232, both herein incorporated by reference. Pharmaceutical compositions of the invention can be administered by, for example, subcutaneous, intravenous, or intramuscular injection, topical or oral administration, large volume parenteral solutions useful as blood substitutes, etc. Pharmaceutical compositions of the invention can be administered by any conventional means such as by oral or aerosol administration, by transdermal or mucus membrane adsorption, or by injection.

For example, the hemoglobins of the present invention can be used in compositions useful as substitutes for red blood cells in any application that red blood cells are used or for any application in which oxygen delivery is desired. Such hemoglobins of the instant invention formulated as red blood cell substitutes can be used for the treatment of hemorrhages, traumas and surgeries where blood volume is lost and either fluid volume or oxygen carrying capacity or both must be replaced. Moreover, because the hemoglobins of the instant invention can be made pharmaceutically acceptable, the hemoglobins of the instant invention can be used not only as blood substitutes that deliver oxygen but also as simple volume expanders that provide oncotic pressure due to the presence of the large hemoglobin protein molecule. In a further embodiment, the crosslinked hemoglobin of the instant invention can be used in situations where it is desirable to limit the extravasation or reduce the colloid osmotic pressure of the hemoglobin-based blood substitute. The hemoglobins of the present invention can be synthesized with a high molecular weight. Thus the hemoglobins of the instant invention can act to transport oxygen as a red blood cell substitute, while reducing the adverse effects that can be associated with excessive extravasation.

A typical dose of the hemoglobins of the instant invention as an oxygen delivery agent can be from 2 mg to 5 grams or more of extracellular hemoglobin per kilogram of patient body weight. Thus, a typical dose for a human patient might be from a few grams to over 350 grams. It will be appreciated that the unit content of active ingredients contained in an individual dose of each dosage form need not in itself constitute an effective amount since the necessary effective amount could be reached by administration of a plurality of administrations as injections, etc. The selection of dosage depends upon the dosage form utilized, the condition being treated, and the particular purpose to be achieved according to the determination of the skilled artisan in the field.

Administration of the hemoglobins of the instant invention can occur for a period of seconds to hours depending on the purpose of the hemoglobin usage. For example, as an oxygen delivery vehicle, the usual time course of administration is as rapid as possible. Typical infusion rates for hemoglobin solutions as blood replacements can be from about 100 ml to 3000 ml/hour.

In a further embodiment, the hemoglobins of the instant invention can be used to treat anemia, both by providing additional oxygen carrying capacity in a patient that is suffering from anemia, and/or by stimulating hematopoiesis as described in PCT publication WO 95/24213. When used to stimulate hematopoiesis, administration rates can be slow because the dosage of hemoglobin is much smaller than dosages that can be required to treat hemorrhage. Therefore the hemoglobins of the instant invention can be used for applications requiring administration to a patient of high volumes of hemoglobin as well as in situations where only a small volume of the hemoglobin of the instant invention is administered.

Because the distribution in the vasculature of the hemoglobins of the instant invention is not limited by the size of the red blood cells, the hemoglobin of the present invention can be used to deliver oxygen to areas that red blood cells cannot penetrate. These areas can include any tissue areas that are located downstream of obstructions to red blood cell flow, such as areas downstream of thrombi, sickle cell occlusions, arterial occlusions, angioplasty balloons, surgical instrumentation, any tissues that are suffering from oxygen starvation or are hypoxic, and the like. Additionally, any types of tissue ischemia can be treated using the hemoglobins of the instant invention. Such tissue ischemias include, for example, stroke, emerging stroke, transient ischemic attacks, myocardial stunning and hibernation, acute or unstable angina, emerging angina, infarct, and the like. Because of the broad distribution in the body, the hemoglobins of the instant invention can also be used to deliver drugs and for in vivo imaging.

The hemoglobins of the instant invention can also be used as replacement for blood that is removed during surgical procedures where the patient's blood is removed and saved for reinfusion at the end of surgery or during recovery (acute normovolemic hemodilution or hemoaugmentation). In addition, the hemoglobins of the instant invention can be used to increase the amount of blood that can be predonated prior to surgery, by acting to replace some of the oxygen carrying capacity that is donated.

The following examples are intended to illustrate, but not limit, the present invention.

EXAMPLE 1

Constructions of Plasmids Containing Mutations in Copy Number: Medium Copy Number Plasmid; pSGE705

Recombinant hemoglobin-like protein (rHb1.1, described in, for example, PCT publication WO 90/13645, incorporated herein by reference) was produced by fermentation of several *E. coli* strains containing modifications of the lac promoter region and/or location. Construction of the parent *E. coli* strain 1661 carrying the plasmid pSGE705 is described in WO 97/04110, published Feb. 6, 1997, and incorporated herein by reference.

EXAMPLE 2

Construction of Plasmids Containing Mutations in Copy Number:

High Copy Number Plasmid, pSGE720

The construction of pSGE720 was performed in two stages. First, the pUC origin of replication was introduced into PSGE705 to create plasmid pSGE715, which is similar to pSGE705 in that it includes the lacI gene. Then, the lacI gene was deleted from the plasmid and replaced with a short oligonucleotide containing several convenient restriction sites to create plasmid pSGE720. The details are provided in WO 97/04110, incorporated herein by reference.

EXAMPLE 3

Construction of Strains Containing Various lacI Chromosomal Alleles: SGE1661, SGE1670 and SGE1675

Strains SGE1494 and SGE1495 which contained lacI$q$ on the chromosome were purchased from ATCC, (ATCC accession numbers 47041 and 47043 respectively). SGE77 was purchased from Stratagene, Inc. (Catalogue number D1210) and also contained a lacI$q$ on an F' episome.

Strain SGE1661 contained a wild type chromosomal lacI allele. This strain was used as the starting material for the construction of strains containing alternative chromosomal lacI alleles.

To examine the effect of increasing the strength of the chromosomal lacI promoter, strain SGE1670 was constructed. Strain SGE1670 containing the lacI$q^1$ allele was constructed from SGE1661 by P1 bacteriophage transduction using a lysate grown on SGE299, selecting for kanamycin resistant transductants. Strain SGE299 contained a putative lacI$q^1$ allele on an F' episome adjacent a lacZ gene into which a Tn5 transposon has been inserted to inactivate lacZ. The transposon insertion conferred kanamycin resistance to the cells. SGE299 is also know as AG1688 or RDK2759 and is described by Hu et al., (Protein Science, 2: 1072–1084, 1993). Alternatively, one skilled in the art could use any strain having a lacI or lacI$q$ allele and mutating the sequence to yield lacI$q^1$ using the sequence of Calos & Miller, *Mol. Gen. Genet.* 183:559–560 (1981) as a guide. PCR analysis of SGE299 (described below) demonstrated that the putative lacI$q$ was lacI$q^1$, or a variant thereof.

In strain SGE1675, the lac operon functionality on the chromosome was restored without affecting the lacI allele. The presence of the transposon insertion in lacZ in SGE1670 resulted in a polar mutation that destroyed the function lacY and lacA involved in lactose metabolism and transport, which may have affected the ability to induce expression of $P_{tac}$ on the plasmid with IPTG, and thus may have affected beta-galactosidase or hemoglobin production from a given plasmid. SGE1675 was constructed by transduction of SGE1670 from a P1 lysate prepared on SGE765. SGE765 was a strain containing a Tn5 insertion into the lacI gene conferring kanamycin resistance to the cells. In addition, SGE765 contained a wild type copy of lacZ. Strain SGE765 was made by P1 transduction from a lysate made on MS24 into strain C3000. MS24 is also known as MG1655 lacI3098:: Tn10$^{kan}$, acZA118, and is described in Singer, et al. (Microbiol. Rev. 53: 1–24, 1989). Strain C3000 is available from the American Type Culture Collection, ATCC # 15597.

Transductants were selected for their ability to grow on minimal medium containing lactose as the sole carbon source and screened for sensitivity to kanamycin. Transductants that were sensitive to kanamycin and were lac$^+$, were screened for their ability to regulate (repress) the expression of beta-galactosidase from plasmid pSGE714 (see below). Note: pSGE714 does not contain a lacI on the plasmid and was examined for repression of lacZ as described for strain SGE1670.

EXAMPLE 4

Medium Copy Number LacZ Fusion Plasmid Containing lacI: pSCE712 pSGE712 containing the lacI gene and a fusion of the lacZ gene to the 5' end of the beta globin gene was constructed as described below. This construct provided a convenient tool for screening control of expression as a function of beta-galactosidase activity in the cells. Thus in the absence of inducer, the expression of beta-galactosidase provided a sensitive measure of control of expression by the product of the lac repressor gene expressed primarily from the plasmid.

pSGE705 was digested with SalI and BglII. pMBL1034 (obtained from Sankar Adhya, NIH, and described in Miller, G. H., Experiments in Gene Fusions, (1984), Cold Spring Harbor Laboratory Press, Cold Spring Harbor, N.Y.) was digested with BamHI and BalI. The two digests were cleaned using a Promega MagicDNA clean-up column using the manufacturer's recommended procedures, and the DNA was ligated using T4 DNA ligase. The ligation mix was used to transform JM109 competent cells. Candidates were ampicillin resistant and blue colonies on LB amp plates containing X-gal and were screened by BamHI/HindIII digestion for the appropriate plasmid conformation. Correct candidates contained a BamHI-HindIII fragment almost 3 Kilobase pairs longer than the original plasmid, indicating the presence of the lacZ gene on the plasmid.

EXAMPLE 5

Construction of a Medium Copy Number LacZ Fusion Plasmid without lacI: pSGE714 pSGE714 containing a fusion of the lacZ gene to the 5' end of the beta globin gene was constructed as described in Example 4, except that pSGE654 was used instead of pSGE705 as the starting material. Note that unlike pSGE712, pSGE714 did not contain lacI. This construct provided a convenient tool for screening control of expression as a function of beta-galactosidase activity in the cells. Thus, in the absence of inducer, the expression of beta-galactosidase provided a sensitive measure of control of expression by the product of the lac repressor gene expressed from the chromosome of the cell.

EXAMPLE 6

Construction of a High Copy Number LacZ Fusion Plasmid without lacI: pSGE721 pSGE721 containing a fusion of the lacZ gene to the 5' end of the beta globin gene was constructed as described in Example 4, except that pSGE720 was used instead of pSGE705 as the starting material. This construct provided a convenient tool for screening control of expression as a function of beta-galactosidase activity in the cells. Thus, in the absence of inducer, the expression of beta-galactosidase provided a sensitive measure of control of expression by the product of the lac repressor gene expressed from the chromosome of the cell. This plasmid results in approximately 500 copies of the plasmid per cell. In order to control the expression of beta-galactosidase from these plasmid copies, more repressor must be expressed from the chromosomal copy of lacI per cell than there are plasmids per cell.

EXAMPLE 7

Construction of a High Copy Number Plasmid Containing a Single Alpha Globin Gene and Wild Type Beta Gene: pSGE728

The construction of pSGE728 was performed by digesting plasmid pSGE720 with an enzyme that cuts only within each of the two alpha subunits of the di-alpha gene encoding the globin-like protein, followed by ligation, to preferentially reconstruct deletions of one alpha subunit, and the di-alpha glycine linker. The resulting plasmid, pSGE726, contains a single alpha gene rather than a di-alpha gene. The Presbyterian mutation of human hemoglobin in the beta globin gene was replaced by a second digestion and ligation that introduced the wild-type beta and created pSGE728.

A. Construction of pSGE726 pSGE720 was digested with restriction enzyme XhoI, according to the manufacturer's instructions (New England Biolabs). The pSGE720 digest was purified with Promega Magic DNA Clean-up protocols and reagents (Promega, Madison, Wis.) and suspended in ligation buffer. T4 DNA ligase was added and the DNA was incubated overnight at 16° C. SGE1675 cells were made competent by the method of Hanahan (Hanahan, D, ibid), and transformed with the ligation mixture according to the referenced protocol. Transformants were selected by plating the cells on LB plates containing 15µg/ml tetracycline. Candidates were screened by restriction digestion to determine the presence of a mono-alpha globin gene, rather than the di-alpha globin gene present in pSGE720. Several candidates were identified, and the resulting plasmid was named pSGE726 in SGE1675 was called SGE1480. This plasmid expressed the hemoglobin-like molecule rHb1.0, mono-alpha plus beta$^P$-$_{resbyterian}$.

B. Construction of pSGE728 pSGE726 and pSGE0.0E4 (Hoffman et al., 1990. Proc. Natl. Acad. Sci. USA. 87:8521–8525 and Looker et al., 1992. Nature, 356:258–260) were digested with restriction enzymes BglII and HindIII, according to the manufacturer's instructions (New England Biolabs). The digests were loaded into wells in a 1% agarose gel, and subjected to electrophoresis in Tris acetate buffer as described in Maniatis et al. (Maniatis, T., E. P. Fritsch, and J. Sambrook. 1982. Molecular Cloning. Cold Spring Harbor Laboratory, Cold Spring Harbor, N.Y.). The small DNA band of about 300 basepairs (bp) from the pSGE0.0E4 digest, and the large band of about 3,400 bp from the pSGE726 digest, were purified by excising them from the agarose gel, pooling them into a 1.7 ml tube and purifying them with GeneClean Kit ptotocols and reagents (BIO 101, La Jolla, Calif.). Purified, pooled DNA fragments were suspended in ligation buffer. T4 DNA ligase was added and the DNA was incubated overnight at 16° C. SGE1675 cells were made competent by the method of Hanahan (Hanahan, D, ibid), and transformed with the ligation mixture according to the referenced ptotocol. Transformants were selected by plating the cells on LB plates containing 15 g/ml tetracycline. Candidates were screened by restriction digestion with Sca I according to the manufacturer's instructions (New England Biolabs), to determine the presence of a wild type beta globin gene, which is not susceptible to ScaI digestion, rather than the beta$^{Presbyterian}$ gene which is cleaved by ScaI. Several candidates were identified. The resulting plasmid was named pSGE728. pSGE728 in SGE1675 was called SGE1483. This plasmid expressed rHb0.0, mono-alpha plus wild type beta.

EXAMPLE 8

Construction of pSGE733 and Plasmids Containing Beta Mutations

Figure 3:
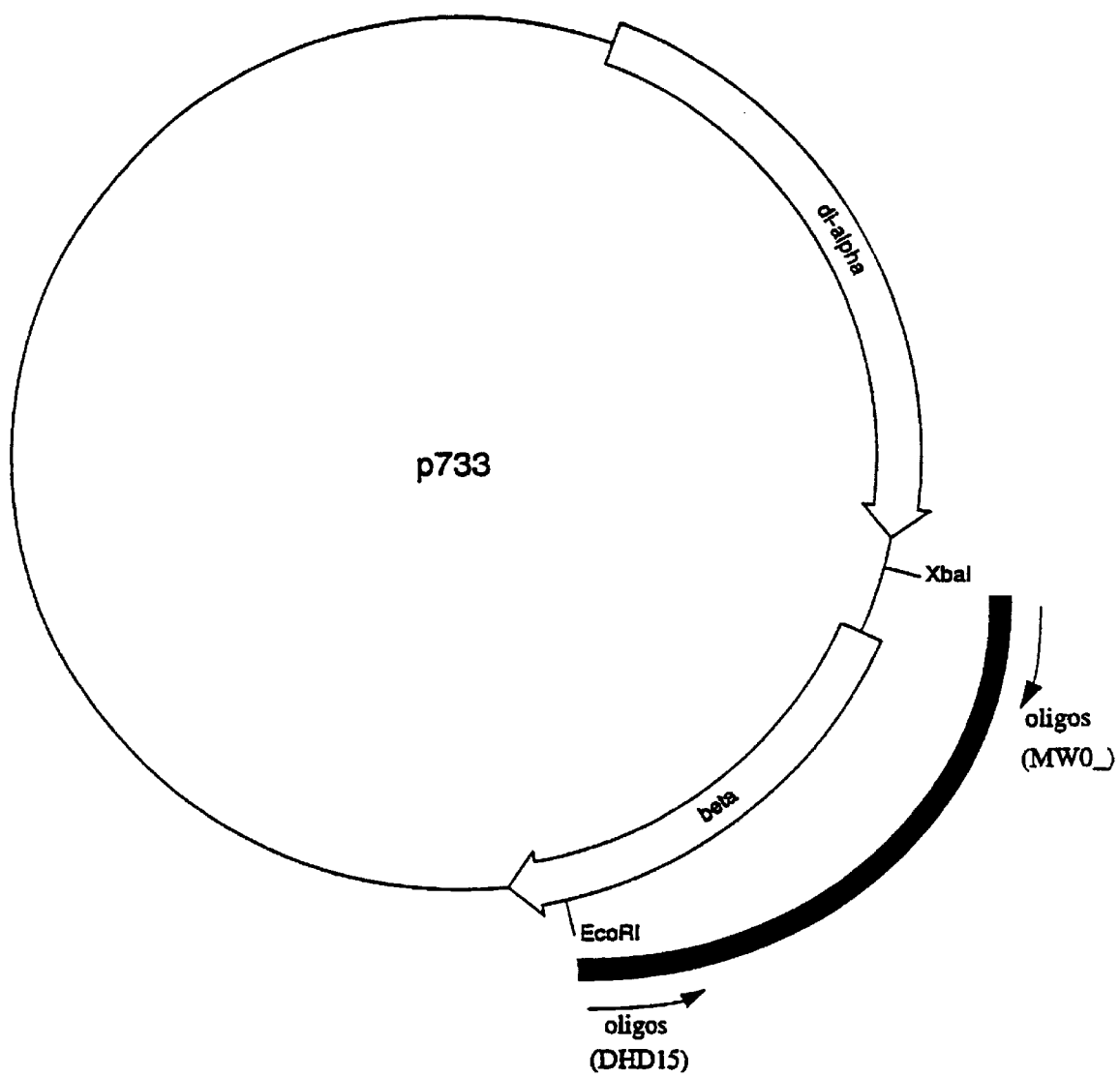
FIG. 3 shows the plasmid for p733.

Plasmid pSGE733 was constructed with the di-alpha gene from pSGE720 and the wild-type beta globin of pSGE728 using methods as described above. This plasmid is depicted in FIG. 3. PCR-directed mutagenesis was used to create the four beta globin variants with amino acid substitutions and/or insertions after the initial methionine. The oligos used to separately introduce the changes into a high copy number plasmid using pSGE733 as the template are identified in Table 1. Oligo DHD15 includes the EcoRI restriction site in beta. The PCR fragments were cleaned with the Promega PCR clean up kit and were thereafter cut with EcoRI and EbaI in a double digest.

1675) to create the strains identified in Table 2. Oligomer MW039 was combined with p539 and the resulting plasmid was used to transform SGE 1675 into SGE 2706. Similarly, MW041 was used to make SGE 3166, MW042 was used to make SGE 3167 and MW043 was used to make SGE 3168.

TABLE 2

| recombinant hemoglobin | beta globin N-terminal seguence (final) |
|---|---|
| SGE 2706 | Met-His-Leu-Thr-Pro-Glu-Glu . . . (SEQ. ID. NO. 8) |
| SGE 3166 | Met-Leu-Leu-Thr-Pro-Glu-Glu . . . (SEQ. ID. NO. 9) |
| SGE 3167 | Ala-His-Leu-Thr-Pro-Glu-Glu . . . (SEQ. ID. NO. 10) |
| SGE 3168 | Ala-Ala-Leu-Thr-Pro-Glu-Glu . . . (SEQ. ID. NO. 11) |

Expression of recombinant hemoglobin in *E.coli* has been previously reported in U.S. Pat. No. 5,028,588, incorporated herein by reference. Hemoglobin expression was induced in cells growing in defined medium supplemented with hemin (0.5 mg/ml) by addition of 100 uM IPTG, followed by 30° C. incubation overnight. All recombinant mutant hemoglobins were purified from the *E.coli* expression strains by a

TABLE 1

OLIGOS

```
MW039:
                               ala                          (SEQ.ID.NO.3)
5' GCT CTA GAT AAG GAG GTA AAT ATA TGG CTC TGA CTC CG 3'
                               met     leu MW041:
                               ala     leu                  (SEQ.ID.NO.4)
5' GCT CTA GAT AAG GAG GTA AAT ATA TGG CTG CTC TGA CTC 3'
                               met     ala MW042:
                               ala     leu                  (SEQ.ID.NO.5)
5' GCT CTA GAT AAG GAG GTA AAT ATA TGG CTC ACC TGA CTC 3'
                               met     his MW043:
                                       leu                  (SEQ.ID.NO.6)
5' GCT CTA GAT AAG GAG GTA AAT ATA TGC TGC TGA CTC CG 3'
                               met     leu DHD15:
5' GGG AAT TCT TTA CCG A 3'                                 (SEQ.ID.NO.7)
```

The digested fragments were separately cloned into high copy number plasmids based on pSGE720 with a non-methylated XbaI site for expression. The non-methylated XbaI site was created by inserting an extra "A" before the first T of the XbaI sequence (ATCTAGA). The resulting plasmid is referred to as p539.

Since the wild type beta of pSGE733 does not contain a ScaI restriction site, unlike pSGE720 which contains a ScaI restriction site, the resulting candidate plasmids were screened by restriction digestion.

EXAMPLE 9

Preparation of Strains SGE 2706, SGE 3166, SGE 3167 and SGE 3168

A. Proteins and Reagents

Four candidate plasmids obtained from Example 8 were used to transform the same *E.coli* background strain (SGE procedure previously reported in Looker et al., *Methods in Enzymology*, 231:364–374 (1994), carbon monoxide liganded and buffer exchanged in 0.1 sodium phosphate (pH 8.3) according to the method described in WO 95/14038, incorporated herein by reference, by Sephadex G25 chromatography. Final primary sequence of each variant was determined by automated Edman sequencing and confirmed by LC-MS analysis.

NiCl$_2$, EDTA, and oxone (potassium peroxymonosulfate) were all purchased from Aldrich.

B. Crosslinking reaction conditions

Crosslinking reactions were carried out in a total volume of 100 uL in 0.1 M sodium phosphate pH 8.3 with final hemoglobin concentration of 0.4mM, final nickel concentration of 0.8 mM. Oxone (Aldrich) was added to a final concentration of 0.8 mM and the reactions placed on ice under argon for one hour. Reactions were then quenched by addition of EDTA to a final concentration of 10 mM.

C. Reversed phase HPLC and SDS PAGE analysis

Hemoglobins were de-hemed by acid acetone extraction and resolubilized in 2% formic acid in water prior to revered phase HPLC. Reversed phase HPLC globin fractions were lyophilised and resolubilized in reducing sample buffer containing 50 mM DTT prior to SDS PAGE analysis on a NOVEX™ 4–20% Tris-Glycine gel.

D. Electrospray Mass Spectrometry

Electrospray mass spectometry (ESMS) was performed using a Finnigan MAT LCQ™ (Finnegan, San Jose, Calif.). Reversed phase HPLC derived fractions were infused in LCQ source at 4 uL/min. in 0.1% TFA/40% acetonitrile in water.

E. Pepsin Mapping

On-line enzymatic digestion-peptide mapping was performed using a Prozyme immobilized pepsin column (PerSeptive Biosystems, Inc., Cambridge, Mass.) employing a variation of an on-line digest/peptide mapping method recently described in Lippincott et al. *ABRF'96: Biomolecular Techniques*, S32 (1996).

The results of the studies are shown in Tables 3 and 4 below. Table 3 shows the effect of amino acid sequences on deamination and crosslinking of the beta globins. Table 4 shows fragment ions of sodium cyanoborohydride reduced crosslink peptides ($\beta_1+\beta_{15,16}$) formed through Schiff's base chemistry between the new free carbonyl on the N-terminus of one beta globin and Lys144 of the second beta globin.

The results of these experiments show reaction of native state hemoglobin in solution with Ni(II) and oxone results in the formation of intramolecular, dimeric beta globin. This reaction is blocked by inclusion of EDTA in the reaction mixture, as well as by substitution of the beta globin His2 by Leu or Ala. These results indicate that the beta globin His2 can serve as a binding site for a high valent nickel complex. This complex is seen to promote a predominatly intramolecular crosslinked beta dimer.

TABLE 4

| Ions ID | m/z Observed | Predicted | Fragment type |
|---|---|---|---|
| 1 | — | 100.1 | $\beta_{15,16}$—$B_1$ |
| 2 | — | 199.1 | $\beta_{15,16}$—$B_2$ |
| 3 | — | 270.2 | $\beta_{15,16}$—$B_3$ |
| 4 | 326.9 | 327.2 | $\beta_{15,16}$—$B_4$ |
| 5 | — | 426.3 | $\beta_{15,16}$—$B_5$ |
| 6 | 497.6 | 497.3 | $\beta_{15,16}$—$B_6$ |
| 7 | 611.4 | 611.3 | $\beta_{15,16}$—$B_7$ |
| 8 | 681.9 | 682.4 | $\beta_{15,16}$—$B_8$ |
| 9 | 795.7 | 795.5 | $\beta_{15,16}$—$B_9$ |
| 10 | 866.4 | 866.5 | $\beta_{15,16}$—$B_{10}$ |
| 11 | 1004.2 | 1003.6 | $\beta_{15,16}$—$B_{11}$ |
| 12 | 751.6 | 752.4(+2) | ($\beta_{15,16}$-17) + $\beta_1$—$B_1$ |
| 13 | 820.8 | 821.0(+2) | ($\beta_{15,16}$-17) + $\beta_1$—$B_2$ |
| 14 | — | 877.5(+2) | ($\beta_{15,16}$-17) + $\beta_1$—$B_3$ |
| 15 | 928.5 | 928.1(+2) | ($\beta_{15,16}$-17) + $\beta_1$—$B_4$ |
| 16 | 975.8 | 976.6(+2) | ($\beta_{15,16}$-17) + $\beta_1$—$B_5$ |
| 17 | 1041.1 | 1041.1(+2) | ($\beta_{15,16}$-17) + $\beta_1$—$B_6$ |
| 18 | 1105.8 | 1105.6(+2) | ($\beta_{15,16}$-17) + $\beta_1$—$B_7$ |
| 19 | — | 147.1 | $\beta$—$Y_1$ |
| 20 | — | 276.2 | $\beta$—$Y_2$ |
| 21 | 404.9 | 405.2 | $\beta$—$Y_3$ |
| 22 | 502.1 | 502.2 | $\beta$—$Y_4$ |
| 23 | 603.3 | 603.3 | $\beta$—$Y_5$ |
| 24 | 717.3 | 716.4 | $\beta$—$Y_6$ |
| 25 | 853.5 | 853.4 | $\beta$—$Y_7$ |
| 26 | 1353.6 | 1354.3 | ($\beta_1$-17) + $\beta_{15,16}$—$Y_3$ |
| 27 | 1490.6, 745.8 | 1491.4, 746.2(+2) | ($\beta_1$-17) + $\beta_{15,16}$—$Y_4$ |
| 28 | 1562.6 | 1562.6 | ($\beta_1$-17) + $\beta_{15,16}$—$Y_5$ |
| 29 | 838.1 | 838.3(+2) | ($\beta_1$-17) + $\beta_{15,16}$—$Y_6$ |
| 30 | 873.5 | 873.8(+2) | ($\beta_1$-17) + $\beta_{15,16}$—$Y_7$ |
| 31 | 930.6 | 930.8(+2) | ($\beta_1$-17) + $\beta_{15,16}$—$Y_8$ |
| 32 | 966.0 | 966.3(+2) | ($\beta_1$-17) + $\beta_{15,16}$—$Y_9$ |
| 33 | 1015.3 | 1015.9(+2) | ($\beta_1$-17) + $\beta_{15,16}$—$Y_{10}$ |
| 34 | 1044.2 | 1044.4(+2) | ($\beta_1$-17) + $\beta_{15,16}$—$Y_{11}$ |
| 35 | 1079.7 | 1079.9(+2) | ($\beta_1$-17) + $\beta_{15,16}$—$Y_{12}$ |
| 36 | 1129.7 | 1129.4(+2) | ($\beta_1$-17) + $\beta_{15,16}$—$Y_{13}$ |

(+2)- indicates double charged ions

TABLE 3

| rHb variants | Beta globin protein sequence (positions) | | | | | | | Deami nation | Cross- link |
|---|---|---|---|---|---|---|---|---|---|
| | −1 | 1 | 2 | | 143 | 144 | 145 | 146 | | |
| rHb69 (SEQ ID NO:12) | | Met | His | ... | His | Lys | Tyr | His | − | ++ |
| rHb68 (SEQ ID NO:13) | | Met | Leu | ... | His | Lys | Tyr | His | − | − |
| rHb67 (SEQ ID NO:14) | met | Ala | His | ... | His | Lys | Tyr | His | + | ++ |
| rHb66 (SEQ ID NO:15) | met | Ala | Ala | ... | His | Lys | Tyr | His | − | − |
| rHb95 (SEQ ID NO:16) | met | Ala | His | ... | Ala | Ala | Tyr | His | + | ++ |
| rHb96 (SEQ ID NO:17) | | Met | His | ... | His | Lys | His | His | + | ++ |
| rHb97 (SEQ ID NO:18) | met | Ala | His | ... | His | Ala | Ala | His | + | ++ |
| rHb98 (SEQ ID NO:19) | met | Ala | His | ... | His | Ala | Tyr | Ala | + | ++ |
| rHb80 (SEQ ID NO:20) | met | Ala | His | ... | His | Lys | Tyr | − | + | ++ |
| rHb81 (SEQ ID NO:21) | met | Ala | His | ... | His | − | − | − | + | + |
| rHb82 (SEQ ID NO:22) | met | Ala | His | ... | − | − | − | − | + | − |

SEQUENCE LISTING

<160> NUMBER OF SEQ ID NOS: 22

<210> SEQ ID NO 1
<211> LENGTH: 141
<212> TYPE: PRT
<213> ORGANISM: HUMAN ALPHA GLOBIN

<400> SEQUENCE: 1

Val Leu Ser Pro Ala Asp Lys Thr Asn Val Lys Ala Ala Trp Gly Lys
 1               5                  10                  15

Val Gly Ala His Ala Gly Glu Tyr Gly Ala Glu Ala Leu Glu Arg Met
             20                  25                  30

Phe Leu Ser Phe Pro Thr Thr Lys Thr Tyr Phe Pro His Phe Asp Leu
         35                  40                  45

Ser His Gly Ser Ala Gln Val Lys Gly His Gly Lys Lys Val Ala Asp
     50                  55                  60

Ala Leu Thr Asn Ala Val Ala His Val Asp Asp Met Pro Asn Ala Leu
 65                  70                  75                  80

Ser Ala Leu Ser Asp Leu His Ala His Lys Leu Arg Val Asp Pro Val
                 85                  90                  95

Asn Phe Lys Leu Leu Ser His Cys Leu Leu Val Thr Leu Ala Ala His
            100                 105                 110

Leu Pro Ala Glu Phe Thr Pro Ala Val His Ala Ser Leu Asp Lys Phe
        115                 120                 125

Leu Ala Ser Val Ser Thr Val Leu Thr Ser Lys Tyr Arg
    130                 135                 140

<210> SEQ ID NO 2
<211> LENGTH: 146
<212> TYPE: PRT
<213> ORGANISM: HUMAN BETA GLOBIN

<400> SEQUENCE: 2

Val His Leu Thr Pro Glu Glu Lys Ser Ala Val Thr Ala Leu Trp Gly
 1               5                  10                  15

Lys Val Asn Val Asp Glu Val Gly Gly Glu Ala Leu Gly Arg Leu Leu
             20                  25                  30

Val Val Tyr Pro Trp Thr Gln Arg Phe Phe Glu Ser Phe Gly Asp Leu
         35                  40                  45

Ser Thr Pro Asp Ala Val Met Gly Asn Pro Lys Val Lys Ala His Gly
     50                  55                  60

Lys Lys Val Leu Gly Ala Phe Ser Asp Gly Leu Ala His Leu Asp Asn
 65                  70                  75                  80

Leu Lys Gly Thr Phe Ala Thr Leu Ser Glu Leu His Cys Asp Lys Leu
                 85                  90                  95

His Val Asp Pro Glu Asn Phe Arg Leu Leu Gly Asn Val Leu Val Cys
            100                 105                 110

Val Leu Ala His His Phe Gly Lys Glu Phe Thr Pro Pro Val Gln Ala
        115                 120                 125

Ala Tyr Gln Lys Val Val Ala Gly Val Ala Asn Ala Leu Ala His Lys
    130                 135                 140

Tyr His
145

<210> SEQ ID NO 3

```
<211> LENGTH: 38
<212> TYPE: DNA
<213> ORGANISM: Artificial Sequence
<220> FEATURE:
<223> OTHER INFORMATION: Description of Artificial Sequence: synthetic
      oligonucleotide used for PCR - directed
      mutagenesis to introduce amino acid modifications
      in the beta globin chain after the intitial
      methionine

<400> SEQUENCE: 3
gctctagata aggaggtaaa tatatggctc tgactccg                              38

<210> SEQ ID NO 4
<211> LENGTH: 39
<212> TYPE: DNA
<213> ORGANISM: Artificial Sequence
<220> FEATURE:
<223> OTHER INFORMATION: Description of Artificial Sequence: synthetic
      oligonucleotide used for PCR - directed
      mutagenesis to introduce amino acid modifications
      in the beta globin chain after the initial
      methionine

<400> SEQUENCE: 4
gctctagata aggaggtaaa tatatggctg ctctgactc                             39

<210> SEQ ID NO 5
<211> LENGTH: 39
<212> TYPE: DNA
<213> ORGANISM: Artificial Sequence
<220> FEATURE:
<223> OTHER INFORMATION: Description of Artificial Sequence: synthetic
      oligonucleotide used for PCR - directed
      mutagenesis to introduct amino acid modifications
      in the beta globin chain after the initial
      methionine

<400> SEQUENCE: 5
gctctagata aggaggtaaa tatatggctc acctgactc                             39

<210> SEQ ID NO 6
<211> LENGTH: 38
<212> TYPE: DNA
<213> ORGANISM: Artificial Sequence
<220> FEATURE:
<223> OTHER INFORMATION: Description of Artificial Sequence: synthetic
      oligonucleotide used for PCR - directed
      mutagenesis to introduce amino acid modifications
      in the beta globin chain after the initial
      methionine

<400> SEQUENCE: 6
gctctagata aggaggtaaa tatatgctgc tgactccg                              38

<210> SEQ ID NO 7
<211> LENGTH: 16
<212> TYPE: DNA
<213> ORGANISM: Artificial Sequence
<220> FEATURE:
<223> OTHER INFORMATION: Description of Artificial Sequence: synthetic
      oligonucleotide used for PCR - directed
      mutagenesis to introduce amino acid modifications
      in the beta globin chain after the intitial
      methionine

<400> SEQUENCE: 7
gggaattctt taccgg                                                     16
```

-continued

```
<210> SEQ ID NO 8
<211> LENGTH: 7
<212> TYPE: PRT
<213> ORGANISM: Escherichia coli

<400> SEQUENCE: 8

Met His Leu Thr Pro Glu Glu
  1               5

<210> SEQ ID NO 9
<211> LENGTH: 7
<212> TYPE: PRT
<213> ORGANISM: Escherichia coli

<400> SEQUENCE: 9

Met Leu Leu Thr Pro Glu Glu
  1               5

<210> SEQ ID NO 10
<211> LENGTH: 7
<212> TYPE: PRT
<213> ORGANISM: Escherichia coli

<400> SEQUENCE: 10

Ala His Leu Thr Pro Glu Glu
  1               5

<210> SEQ ID NO 11
<211> LENGTH: 7
<212> TYPE: PRT
<213> ORGANISM: Escherichia coli

<400> SEQUENCE: 11

Ala Ala Leu Thr Pro Glu Glu
  1               5

<210> SEQ ID NO 12
<211> LENGTH: 146
<212> TYPE: PRT
<213> ORGANISM: Escherichia coli

<400> SEQUENCE: 12

Met His Leu Thr Pro Glu Glu Lys Ser Ala Val Thr Ala Leu Trp Gly
  1               5                  10                  15

Lys Val Asn Val Asp Glu Val Gly Gly Glu Ala Leu Gly Arg Leu Leu
             20                  25                  30

Val Val Tyr Pro Trp Thr Gln Arg Phe Phe Glu Ser Phe Gly Asp Leu
         35                  40                  45

Ser Thr Pro Asp Ala Val Met Gly Asn Pro Lys Val Lys Ala His Gly
     50                  55                  60

Lys Lys Val Leu Gly Ala Phe Ser Asp Gly Leu Ala His Leu Asp Asn
 65                  70                  75                  80

Leu Lys Gly Thr Phe Ala Thr Leu Ser Glu Leu His Cys Asp Lys Leu
                 85                  90                  95

His Val Asp Pro Glu Asn Phe Arg Leu Leu Gly Asn Val Leu Val Cys
            100                 105                 110

Val Leu Ala His His Phe Gly Lys Glu Phe Thr Pro Pro Val Gln Ala
        115                 120                 125

Ala Tyr Gln Lys Val Val Ala Gly Val Ala Asn Ala Leu Ala His Lys
    130                 135                 140

Tyr His
```

```
<210> SEQ ID NO 13
<211> LENGTH: 146
<212> TYPE: PRT
<213> ORGANISM: Escherichia coli

<400> SEQUENCE: 13

Met Leu Leu Thr Pro Glu Glu Lys Ser Ala Val Thr Ala Leu Trp Gly
 1               5                  10                  15

Lys Val Asn Val Asp Glu Val Gly Gly Glu Ala Leu Gly Arg Leu Leu
             20                  25                  30

Val Val Tyr Pro Trp Thr Gln Arg Phe Phe Glu Ser Phe Gly Asp Leu
         35                  40                  45

Ser Thr Pro Asp Ala Val Met Gly Asn Pro Lys Val Lys Ala His Gly
     50                  55                  60

Lys Lys Val Leu Gly Ala Phe Ser Asp Gly Leu Ala His Leu Asp Asn
 65                  70                  75                  80

Leu Lys Gly Thr Phe Ala Thr Leu Ser Glu Leu His Cys Asp Lys Leu
                 85                  90                  95

His Val Asp Pro Glu Asn Phe Arg Leu Leu Gly Asn Val Leu Val Cys
            100                 105                 110

Val Leu Ala His His Phe Gly Lys Glu Phe Thr Pro Pro Val Gln Ala
        115                 120                 125

Ala Tyr Gln Lys Val Val Ala Gly Val Ala Asn Ala Leu Ala His Lys
    130                 135                 140

Tyr His
145

<210> SEQ ID NO 14
<211> LENGTH: 147
<212> TYPE: PRT
<213> ORGANISM: Escherichia coli
<220> FEATURE:
<221> NAME/KEY: NON_TER
<222> LOCATION: (1)
<223> OTHER INFORMATION: the N-terminal methionine residue incorporated
      during the translation initiation step is excised
      during translation and is not present in the
      mature polypeptide chain

<400> SEQUENCE: 14

Met Ala His Leu Thr Pro Glu Glu Lys Ser Ala Val Thr Ala Leu Trp
 1               5                  10                  15

Gly Lys Val Asn Val Asp Glu Val Gly Gly Glu Ala Leu Gly Arg Leu
             20                  25                  30

Leu Val Val Tyr Pro Trp Thr Gln Arg Phe Phe Glu Ser Phe Gly Asp
         35                  40                  45

Leu Ser Thr Pro Asp Ala Val Met Gly Asn Pro Lys Val Lys Ala His
     50                  55                  60

Gly Lys Lys Val Leu Gly Ala Phe Ser Asp Gly Leu Ala His Leu Asp
 65                  70                  75                  80

Asn Leu Lys Gly Thr Phe Ala Thr Leu Ser Glu Leu His Cys Asp Lys
                 85                  90                  95

Leu His Val Asp Pro Glu Asn Phe Arg Leu Leu Gly Asn Val Leu Val
            100                 105                 110

Cys Val Leu Ala His His Phe Gly Lys Glu Phe Thr Pro Pro Val Gln
        115                 120                 125
```

```
Ala Ala Tyr Gln Lys Val Val Ala Gly Val Ala Asn Ala Leu Ala His
        130                 135                 140

Lys Tyr His
145

<210> SEQ ID NO 15
<211> LENGTH: 147
<212> TYPE: PRT
<213> ORGANISM: Escherichia coli
<220> FEATURE:
<221> NAME/KEY: NON_TER
<222> LOCATION: (1)
<223> OTHER INFORMATION: the N-terminal methionine residue incorporated
      during the translation initiation step is excised
      during translation and is not present in the
      mature polypeptide chain

<400> SEQUENCE: 15

Met Ala Ala Leu Thr Pro Glu Glu Lys Ser Ala Val Thr Ala Leu Trp
  1               5                  10                  15

Gly Lys Val Asn Val Asp Glu Val Gly Gly Glu Ala Leu Gly Arg Leu
                 20                  25                  30

Leu Val Val Tyr Pro Trp Thr Gln Arg Phe Phe Glu Ser Phe Gly Asp
             35                  40                  45

Leu Ser Thr Pro Asp Ala Val Met Gly Asn Pro Lys Val Lys Ala His
         50                  55                  60

Gly Lys Lys Val Leu Gly Ala Phe Ser Asp Gly Leu Ala His Leu Asp
 65                  70                  75                  80

Asn Leu Lys Gly Thr Phe Ala Thr Leu Ser Glu Leu His Cys Asp Lys
                 85                  90                  95

Leu His Val Asp Pro Glu Asn Phe Arg Leu Leu Gly Asn Val Leu Val
            100                 105                 110

Cys Val Leu Ala His His Phe Gly Lys Glu Phe Thr Pro Pro Val Gln
        115                 120                 125

Ala Ala Tyr Gln Lys Val Val Ala Gly Val Ala Asn Ala Leu Ala His
    130                 135                 140

Lys Tyr His
145

<210> SEQ ID NO 16
<211> LENGTH: 147
<212> TYPE: PRT
<213> ORGANISM: Escherichia coli
<220> FEATURE:
<221> NAME/KEY: NON_TER
<222> LOCATION: (1)
<223> OTHER INFORMATION: the N-terminal methionine residue incorporated
      during the translation initiation step is excised
      during translation and is not present in the
      mature polypeptide chain

<400> SEQUENCE: 16

Met Ala His Leu Thr Pro Glu Glu Lys Ser Ala Val Thr Ala Leu Trp
  1               5                  10                  15

Gly Lys Val Asn Val Asp Glu Val Gly Gly Glu Ala Leu Gly Arg Leu
                 20                  25                  30

Leu Val Val Tyr Pro Trp Thr Gln Arg Phe Phe Glu Ser Phe Gly Asp
             35                  40                  45

Leu Ser Thr Pro Asp Ala Val Met Gly Asn Pro Lys Val Lys Ala His
         50                  55                  60

Gly Lys Lys Val Leu Gly Ala Phe Ser Asp Gly Leu Ala His Leu Asp
```

```
                65                  70                  75                  80
Asn Leu Lys Gly Thr Phe Ala Thr Leu Ser Glu Leu His Cys Asp Lys
                        85                  90                  95
Leu His Val Asp Pro Glu Asn Phe Arg Leu Leu Gly Asn Val Leu Val
                100                 105                 110
Cys Val Leu Ala His His Phe Gly Lys Glu Phe Thr Pro Pro Val Gln
            115                 120                 125
Ala Ala Tyr Gln Lys Val Val Ala Gly Val Ala Asn Ala Leu Ala Ala
        130                 135                 140
Ala Tyr His
145

<210> SEQ ID NO 17
<211> LENGTH: 146
<212> TYPE: PRT
<213> ORGANISM: Escherichia coli

<400> SEQUENCE: 17

Met His Leu Thr Pro Glu Glu Lys Ser Ala Val Thr Ala Leu Trp Gly
  1               5                  10                  15
Lys Val Asn Val Asp Glu Val Gly Gly Glu Ala Leu Gly Arg Leu Leu
                 20                  25                  30
Val Val Tyr Pro Trp Thr Gln Arg Phe Phe Glu Ser Phe Gly Asp Leu
             35                  40                  45
Ser Thr Pro Asp Ala Val Met Gly Asn Pro Lys Val Lys Ala His Gly
         50                  55                  60
Lys Lys Val Leu Gly Ala Phe Ser Asp Gly Leu Ala His Leu Asp Asn
 65                  70                  75                  80
Leu Lys Gly Thr Phe Ala Thr Leu Ser Glu Leu His Cys Asp Lys Leu
                     85                  90                  95
His Val Asp Pro Glu Asn Phe Arg Leu Leu Gly Asn Val Leu Val Cys
                100                 105                 110
Val Leu Ala His His Phe Gly Lys Glu Phe Thr Pro Pro Val Gln Ala
            115                 120                 125
Ala Tyr Gln Lys Val Val Ala Gly Val Ala Asn Ala Leu Ala His Lys
        130                 135                 140
His His
145

<210> SEQ ID NO 18
<211> LENGTH: 147
<212> TYPE: PRT
<213> ORGANISM: Escherichia coli
<220> FEATURE:
<221> NAME/KEY: NON_TER
<222> LOCATION: (1)
<223> OTHER INFORMATION: the N-terminal methionine residue incorporated
      during the translation intiation step is excised
      during the translation and is not present in the
      mature polypeptide chain

<400> SEQUENCE: 18

Met Ala His Leu Thr Pro Glu Glu Lys Ser Ala Val Thr Ala Leu Trp
  1               5                  10                  15
Gly Lys Val Asn Val Asp Glu Val Gly Gly Glu Ala Leu Gly Arg Leu
                 20                  25                  30
Leu Val Val Tyr Pro Trp Thr Gln Arg Phe Phe Glu Ser Phe Gly Asp
             35                  40                  45
```

```
Leu Ser Thr Pro Asp Ala Val Met Gly Asn Pro Lys Val Lys Ala His
        50                  55                  60

Gly Lys Lys Val Leu Gly Ala Phe Ser Asp Gly Leu Ala His Leu Asp
 65                  70                  75                  80

Asn Leu Lys Gly Thr Phe Ala Thr Leu Ser Glu Leu His Cys Asp Lys
                85                  90                  95

Leu His Val Asp Pro Glu Asn Phe Arg Leu Leu Gly Asn Val Leu Val
            100                 105                 110

Cys Val Leu Ala His His Phe Gly Lys Glu Phe Thr Pro Pro Val Gln
        115                 120                 125

Ala Ala Tyr Gln Lys Val Val Ala Gly Val Ala Asn Ala Leu Ala His
        130                 135                 140

Ala Ala His
145

<210> SEQ ID NO 19
<211> LENGTH: 147
<212> TYPE: PRT
<213> ORGANISM: Escherichia coli
<220> FEATURE:
<221> NAME/KEY: NON_TER
<222> LOCATION: (1)
<223> OTHER INFORMATION: the N-terminal methionine residue incorporated
      during the translation intiation step is excised
      during translation and is not present in the
      mature polypeptide chain

<400> SEQUENCE: 19

Met Ala His Leu Thr Pro Glu Glu Lys Ser Ala Val Thr Ala Leu Trp
 1               5                  10                  15

Gly Lys Val Asn Val Asp Glu Val Gly Gly Glu Ala Leu Gly Arg Leu
                20                  25                  30

Leu Val Val Tyr Pro Trp Thr Gln Arg Phe Phe Glu Ser Phe Gly Asp
            35                  40                  45

Leu Ser Thr Pro Asp Ala Val Met Gly Asn Pro Lys Val Lys Ala His
        50                  55                  60

Gly Lys Lys Val Leu Gly Ala Phe Ser Asp Gly Leu Ala His Leu Asp
 65                  70                  75                  80

Asn Leu Lys Gly Thr Phe Ala Thr Leu Ser Glu Leu His Cys Asp Lys
                85                  90                  95

Leu His Val Asp Pro Glu Asn Phe Arg Leu Leu Gly Asn Val Leu Val
            100                 105                 110

Cys Val Leu Ala His His Phe Gly Lys Glu Phe Thr Pro Pro Val Gln
        115                 120                 125

Ala Ala Tyr Gln Lys Val Val Ala Gly Val Ala Asn Ala Leu Ala His
        130                 135                 140

Ala Tyr Ala
145

<210> SEQ ID NO 20
<211> LENGTH: 146
<212> TYPE: PRT
<213> ORGANISM: Escherichia coli
<220> FEATURE:
<221> NAME/KEY: NON_TER
<222> LOCATION: (1)
<223> OTHER INFORMATION: the N-terminal methionine residue incorporated
      during the translation intiation step is excised
      during translation and is not present in the
      mature polypeptide chain
```

```
-continued

<400> SEQUENCE: 20

Met Ala His Leu Thr Pro Glu Glu Lys Ser Ala Val Thr Ala Leu Trp
 1               5                  10                  15

Gly Lys Val Asn Val Asp Glu Val Gly Gly Glu Ala Leu Gly Arg Leu
             20                  25                  30

Leu Val Val Tyr Pro Trp Thr Gln Arg Phe Phe Glu Ser Phe Gly Asp
         35                  40                  45

Leu Ser Thr Pro Asp Ala Val Met Gly Asn Pro Lys Val Lys Ala His
     50                  55                  60

Gly Lys Lys Val Leu Gly Ala Phe Ser Asp Gly Leu Ala His Leu Asp
 65                  70                  75                  80

Asn Leu Lys Gly Thr Phe Ala Thr Leu Ser Glu Leu His Cys Asp Lys
                 85                  90                  95

Leu His Val Asp Pro Glu Asn Phe Arg Leu Leu Gly Asn Val Leu Val
            100                 105                 110

Cys Val Leu Ala His His Phe Gly Lys Glu Phe Thr Pro Pro Val Gln
        115                 120                 125

Ala Ala Tyr Gln Lys Val Val Ala Gly Val Ala Asn Ala Leu Ala His
    130                 135                 140

Lys Tyr
145

<210> SEQ ID NO 21
<211> LENGTH: 144
<212> TYPE: PRT
<213> ORGANISM: Escherichia coli
<220> FEATURE:
<221> NAME/KEY: NON_TER
<222> LOCATION: (1)
<223> OTHER INFORMATION: the N-terminal methionine residue incorporated
      during the translation initiation step is excised
      during the translation and is not present in the
      mature polypeptide chain

<400> SEQUENCE: 21

Met Ala His Leu Thr Pro Glu Glu Lys Ser Ala Val Thr Ala Leu Trp
 1               5                  10                  15

Gly Lys Val Asn Val Asp Glu Val Gly Gly Glu Ala Leu Gly Arg Leu
             20                  25                  30

Leu Val Val Tyr Pro Trp Thr Gln Arg Phe Phe Glu Ser Phe Gly Asp
         35                  40                  45

Leu Ser Thr Pro Asp Ala Val Met Gly Asn Pro Lys Val Lys Ala His
     50                  55                  60

Gly Lys Lys Val Leu Gly Ala Phe Ser Asp Gly Leu Ala His Leu Asp
 65                  70                  75                  80

Asn Leu Lys Gly Thr Phe Ala Thr Leu Ser Glu Leu His Cys Asp Lys
                 85                  90                  95

Leu His Val Asp Pro Glu Asn Phe Arg Leu Leu Gly Asn Val Leu Val
            100                 105                 110

Cys Val Leu Ala His His Phe Gly Lys Glu Phe Thr Pro Pro Val Gln
        115                 120                 125

Ala Ala Tyr Gln Lys Val Val Ala Gly Val Ala Asn Ala Leu Ala His
    130                 135                 140

<210> SEQ ID NO 22
<211> LENGTH: 143
<212> TYPE: PRT
<213> ORGANISM: Escherichia coli
```

```
<220> FEATURE:
<221> NAME/KEY: NON_TER
<222> LOCATION: (1)
<223> OTHER INFORMATION: the N-terminal methionine residue incorporated
      during the translation initiation step is excised
      during translation and is not present in the
      mature polypeptide chain

<400> SEQUENCE: 22

Met Ala His Leu Thr Pro Glu Glu Lys Ser Ala Val Thr Ala Leu Trp
 1               5                  10                  15

Gly Lys Val Asn Val Asp Glu Val Gly Gly Glu Ala Leu Gly Arg Leu
            20                  25                  30

Leu Val Val Tyr Pro Trp Thr Gln Arg Phe Phe Glu Ser Phe Gly Asp
        35                  40                  45

Leu Ser Thr Pro Asp Ala Val Met Gly Asn Pro Lys Val Lys Ala His
    50                  55                  60

Gly Lys Lys Val Leu Gly Ala Phe Ser Asp Gly Leu Ala His Leu Asp
65                  70                  75                  80

Asn Leu Lys Gly Thr Phe Ala Thr Leu Ser Glu Leu His Cys Asp Lys
                85                  90                  95

Leu His Val Asp Pro Glu Asn Phe Arg Leu Leu Gly Asn Val Leu Val
            100                 105                 110

Cys Val Leu Ala His His Phe Gly Lys Glu Phe Thr Pro Pro Val Gln
        115                 120                 125

Ala Ala Tyr Gln Lys Val Val Ala Gly Val Ala Asn Ala Leu Ala
    130                 135                 140
```

We claim:

1. A method of controlling beta dimer formation in a hemoglobin composition, comprising altering a metal binding site on a beta globin to prevent or reduce said beta dimer formation.

2. The method of claim 1, wherein altering said metal binding site is by substituting a non-metal binding amino acid for the metal binding site.

3. The method of claim 1, wherein said metal binding site is a nickel binding site.

4. The method of claim 3, wherein said nickel binding site is a histidine adjacent to the N-terminus of said beta globin.

5. The method of claim 4, wherein the histidine is substituted with leucine.

6. The method of claim 4, wherein the histidine is substituted with alanine.

7. The method of claim 1, wherein altering said metal binding site is by inserting one or more amino acids between the N-terminus and the metal binding site.

8. The method of claim 7, wherein the metal binding site is a nickel binding site.

9. The method of claim 8, wherein the nickel binding site is a histidine adjacent to the N-terminus of said beta globin prior to said alteration.

10. The method of claim 9, wherein the amino acid to be inserted does not direct N-terminal Met removal when said hemoglobin is expressed in *E. coli*.

11. A method of producing intramolecularly crosslinked globin dimers, comprising adding Ni(II) and oxone to a hemoglobin solution, wherein said hemoglobin contains a globin having a nickel binding site adjacent to the N-terminus of said globin.

12. The method of claim 11, wherein said globin is a beta globin to produce intramolecularly crosslinked beta dimers.

13. The method of claim 12, wherein said nickel binding site is histidine.

* * * * *